United States Patent [19]

Larsson et al.

US005529986A

[11] Patent Number: 5,529,986
[45] Date of Patent: Jun. 25, 1996

[54] CONJUGATE, ITS PREPARATION AND USE AND A SUBSTRATE PREPARED WITH THE CONJUGATE

[75] Inventors: Rolf Larsson; David Westberg; Birgitta Formgren; Anders Uhlin, all of Uppsala, Sweden

[73] Assignee: Corline Systems AB, Uppsala, Sweden

[21] Appl. No.: 211,224

[22] PCT Filed: Sep. 25, 1992

[86] PCT No.: PCT/SE92/00672

§ 371 Date: May 25, 1994

§ 102(e) Date: May 25, 1994

[87] PCT Pub. No.: WO93/05793

PCT Pub. Date: Apr. 1, 1993

[30] Foreign Application Priority Data

Sep. 26, 1991 [SE] Sweden ................... 9102798

[51] Int. Cl.$^6$ .................. A61K 31/725; A61L 33/00
[52] U.S. Cl. ............... 514/54; 514/55; 514/56; 514/822; 536/20; 536/21; 536/18.7; 536/124; 424/422; 424/423; 424/427
[58] Field of Search ............... 514/54, 55, 56; 536/822, 20, 21, 124, 18.7; 424/422, 423, 427

[56] References Cited

U.S. PATENT DOCUMENTS

| 3,810,781 | 5/1974 | Eriksson et al. | 514/56 |
| 4,118,485 | 10/1978 | Eriksson et al. | 514/56 |
| 4,239,664 | 12/1980 | Teng et al. | 525/54.2 |
| 4,415,490 | 11/1983 | Joh | 525/54.2 |
| 4,613,665 | 9/1986 | Larm | 536/20 |
| 4,923,980 | 5/1990 | Blomberg | 536/55.3 |

FOREIGN PATENT DOCUMENTS

| 0212933 | 3/1987 | European Pat. Off. . |
| 0294905 | 12/1988 | European Pat. Off. . |
| 0344068 | 11/1989 | European Pat. Off. . |
| 0351314 | 1/1990 | European Pat. Off. . |
| 8700060 | 1/1987 | WIPO . |

OTHER PUBLICATIONS

Larm., Larson, Olsson. "A New Non-thrombogenic surface prepared by Selective Covalent Binding of Heparin via a Modified Reducing Terminal Residue." Marcel Dekker, Inc. 1984.

*Primary Examiner*—Douglas W. Robinson
*Assistant Examiner*—Kathleen Kahler Fonda
*Attorney, Agent, or Firm*—Birch, Stewart, Kolasch & Birch

[57] ABSTRACT

The present invention relates to a water-soluble conjugate having antithrombin-binding activity comprising a substantially straight-chained organic polymer backbone having at least 30 molecules of sulfated glycosaminoglycans distributed along the polymer backbone, wherein the sulfated glycosaminoglycans are attached to the polymer backbone at a single point of attachment which is not responsible for the antithrombin-binding activity. The present invention also relates to a surface having antithrombin-binding properties prepared with the conjugate and methods of preparing said conjugate and said surface.

13 Claims, No Drawings

CONJUGATE, ITS PREPARATION AND USE AND A SUBSTRATE PREPARED WITH THE CONJUGATE

The present invention relates to a novel biologically active conjugate based upon sulphated glycosaminoglycan, a process of preparing the conjugate, a substrate whose surface has been prepared with such a conjugate, and a process of surface-preparation using the conjugate.

Sulphated glycosaminoglycans is the common name of a number of endogenous sulphated mucopolysaccharides, such as e.g. heparin, heparan sulphate, dermatan sulphate and chondroitin sulphate, which exhibit a number of different biological properties. While the invention relates to sulphated glycosaminoglycans generally, it will, however, in the following to a great extent be described with regard to the glycosaminoglycan that has so far found the greatest medical use, viz. heparin.

Heparin occurs naturally complex-bound to protein in various mammalian tissues, such as the intestine, liver and lung, as well as in mast cells, and has then a molecular weight which may extend up to 100,000, while commercially available preparations have a molecular weight varying between about 6,000 and 20,000 depending on the source and the determination method. It consists of alternating glucuronic acid and glucosamine units, and the anti-coagulating effect has been shown to be linked to a specific pentasaccharide unit of the molecule which has antithrombin-binding properties.

Due to its anti-coagulating properties, heparin, which is usually prepared from intestinal mucosa from pig, has found use as an agent for dissolving thromboses, but perhaps above all for preventing the formation thereof. The latter is the case for inter alia procedures in, for example, the treatment of renal disease, open cardiac surgery and intensive care, which procedures involve treating the patient's blood in a circulating system outside the body, so-called extra-corporeal circulation (e.g. artificial kidneys, heart-lung machines, oxygenators), where the blood will get in contact with various materials foreign to the body.

To eliminate the clotting ability of the blood in such systems, and thereby avoid clogging by blood clots, high doses of heparin must be added to the blood. Due to the accompanying substantially increased risk of bleeding, which in the worst case may lead to life-threatening conditions, efforts have for a long time past aimed at trying to instead achieve the desired coagulation preventing effect by modifying the body-foreign material with which the blood will get in contact by surface-binding heparin thereto. Decisive factors which have stimulated this development are that the structure-activity relation of heparin has been elucidated, and that a heparin-like activity has been detected on the natural vascular wall. Thus, during the last few years several reports on successful extra-corporeal treatment with systems provided with surface-bound heparin have been published.

The surface-modification with heparin has, however, not been restricted the above mentioned contexts with extra-corporeal blood circulation, but has also come to be regarded as a more general solution to the problem of achieving biocompatibility of various devices within medical care which get in contact with blood and other body tissues. For example, surface-heparinization has also been used to improve the biocompatibility of intraocular lenses.

The hitherto used technical solutions to the problem of immobilizing heparin may be divided into two main principles, ionically and covalently bound heparin, which will be described in more detail in the following. To accomplish a surface which exhibits the desired biocompatibility based on immobilized heparin, it is important that heparin is immobilized such that its biological activity is maintained. As mentioned in the introductory part, the biological activity of heparin resides in a specific antithrombin-binding pentasaccharide structure which must remain intact after the immobilization on the surface to be capable of interacting with the constituents of the blood. In the majority of scientific articles and patents related to immobilization of heparin, in particular those published earlier than 1980, this aspect has not been satisfied, and much less have results been presented which makes it possible to judge whether the preparation method will lead to a perfect biocompatible surface. Hereinafter a review of previously known methods of immobilizing heparin is given.

I. IONICALLY BOUND HEPARIN

Since heparin contains a great number of negatively charged groups, the heparin molecule is capable of binding relatively strongly to cationic surfaces through only electrostatic interaction. A common procedure consists in precipitating heparin from an aqueous solution thereof with a cationic surfactant, and subsequently dissolving the dried precipitate with an organic solvent. The latter solvent is then used for a so-called dip-dry procedure. Various branched surfactants have been tested in order to reduce the release rate. Other methods are based upon adsorption of heparin to quaternary ammonium groups. A great disadvantage which the ionic bound heparin surfaces have in common is that their stability with regard to the release of heparin in contact with blood is insufficient.

O. Larm et al. describes in Biomat., Med. Dev., Art. Org., 11 (1983) 161–173 inter alia a method of preparing a stable ionically bound surface. The bound heparin is, however, reported to have lost its biological activity, which may be related to the fact that each individual heparin molecule was bound too strongly such that the antithrombin binding sequence could not interact with circulating components in blood.

A stabilizing treatment of an ionically bound heparin complex with glutaraldehyde has been described in U.S. Pat. No. 3,810,781 and U.S. Pat. No. 4,118,485. As appears from scientific reports, these preparation alternatives do not lead to completely stable surfaces. Thus, heparin and probably various reaction products with glutaraldehyde are released to the blood path during the initial contact phase.

II. COVALENTLY BOUND HEPARIN

From a purely chemical viewpoint there are a number of different ways of immobilizing heparin with covalent bonds. With cyanogen bromide, carbodiimide and similar generally used coupling reagents there is, however, an obvious risk that each heparin molecule will be bound by several bonds including bonds in the active sequence, and that the heparin thereby will lose its biological activity. Covalent coupling reagents are besides always toxic as such and should therefore not get into contact with the final product.

U.S. Pat. No. 4,613,665 describes, however, a method of coupling heparin and other polysaccharides via a single reactive aldehyde group located terminally in the heparin molecule. Hereby heparin may be bound covalently without the antithrombin-binding sequence being involved in coupling. However, the method requires that heparin is partially degraded and that the strongly toxic substance cyanoborohydride is present in the final preparation step.

EP-A-351,314 describes a method of coupling heparin to substrate surfaces containing free amino groups (through treatment of the surface with e.g. polyethylenimine or chitosan) by utilizing free amino groups of heparin which have been subjected to N-desulphation. Cross-linking is then performed with polyfunctional aldehydes, such as e.g. glutaraldehyde. The reaction step with glutaraldehyde can, however, not be controlled with certainty to prevent the active sequence from being involved, and the method as such is relatively complicated to carry out from the technical point of view.

U.S. Pat. No. 4,239,664 describes a PVP-heparin polymer prepared through modification of PVP such that the polymer contains imidoyl ions which then are reacted with hydroxyl groups on heparin. The method necessarily gives multiple non-specific bonds to the heparin, detrimentally effecting the biological activity thereof. The PVP-heparin polymer is consistently said to have a low anti-coagulating activity.

EP-A-294 905 discloses a polymer substrate having an anticoagulant like heparin linked thereto via a polyacid. The substrate is prepared by covalently binding the polyacid to a small number of reactive groups on the polymer surface to thereby multiply the number of available surface reactive groups. The anticoagulant is then covalently coupled to carboxyl or amino groups of the polyacid, specifically by the method described in the above-mentioned U.S. Pat. No. 4,613,665, the disadvantages of which has already been mentioned.

U.S. Pat. No. 4,415,490 discloses a non-thrombogenic material wherein heparin is coupled to various polymers through only one acetal or hemiacetal bond at each binding site. In one embodiment, aldehyde groups are introduced into a polymer, such as cellulose, which aldehyde groups then are reacted with hydroxyl groups in heparin. This process will involve a plurality of the hydroxyl groups of each heparin molecule, and since hydroxyl groups are available in the biologically active sequence of heparin, which sequence was not actually known and described in the literature on the filing date of the patent, there is an apparent risk that also hydroxyl groups in the active sequence will be involved, resulting in the final product being inactive. In an alternative embodiment, aldehyde groups are instead introduced into the heparin by periodation. Also this embodiment lacks specificity, and binding will therefore occur randomly in the heparin chain, including the active sequence.

As will appear from the above, the methods known so far for surface-heparinization thus suffer from more or less serious disadvantages. There is therefore a need for a method of surface-heparinization which is simple to perform and which provides a stable heparinized surface free from toxic substances and with retained biological activity of the heparin.

Also the use of heparin as a therapeutical agent has limitations due to the short half-life and/or affinity of heparin. This is particularly the case for the use of heparin as an anticoagulant, but also, for example, its studied use as a growth inhibitor of smooth muscle cells in case of vessel damages (hyperplasia), as an anti-inflammatory agent for e.g. rheumatoid arthritis, and as an agent for controlling the formation of blood vessels (angiogenesis). A review of the different properties of heparin is to be found in "Heparin: Clinical and biological properties. Clinical applications." Eds: Lane and Lindahl, Edward Arnold, London, 1989. There is therefore a need of heparin preparations having a prolonged half-life and increased affinity.

According to the present invention a novel biologically active conjugate is suggested based upon sulphated glycosaminoglycans, by means of which conjugate the properties of the sulphated glycosaminoglycans may be utilized considerably more efficiently than with the individual substances. Such a conjugate may inter alia easily be made to bind stably to a substrate surface having affinity to the conjugate and may thereby, for example, in the case of heparin be used for simpler and more efficient surface-heparinization than with previous methods. Further, such a conjugate may provide glycosaminoglycan preparations having a longer half-life and an improved affinity compared with preparations based upon the pure substances.

As already mentioned for heparin, the sulphated glycosaminoglycans exist naturally bound to proteins. Thus, for example, in the case of heparin, about 15 heparin chains are bound to a protein of about 25 amino acid residues, while a proteoglycan containing heparan sulphate has fewer and considerably more sparsely arranged heparan sulphate chains. The natural conjugates are very difficult to prepare in pure form and have as far as we know not been suggested for therapeutical or similar use. The invention is based upon the concept of providing a semi- or fully-synthetic conjugate between sulphated glycosaminoglycans and a polymeric carrier, which conjugate, inter alia by containing more molecules of the glycosaminoglycan in question, has improved properties in relation to the individual glycosaminoglycans as well as the natural conjugates, and which conjugate further has the important advantage that the relative composition may be varied in a controllable way to suit different applications.

In its broadest scope the present invention thus provides an at least substantially water-soluble, biologically active conjugate (macromolecule), preferably in substantially pure form, comprising a substantially straight-chained organic homo- or heteropolymer having a number of functional groups distributed along the polymer backbone chain, via which groups at least about 20 molecules from the group of sulphated glycosaminoglycans (GAG) in a non-active part thereof are anchored through covalent bonds.

Such a conjugate may conceptually be described as a synthetic proteoglycan, the relative composition of which may be varied in a controllable way and adapted to the intended application.

The expression "sulphated glycosaminoglycans" herein is meant to comprise not only the substances which are normally included in the term, such as e.g. heparin, heparan sulphate, dermatan sulphate and chondroitin sulphate, but also fragments and derivatives of these substances which are functional for the purpose.

The substantially linear polymer chain which is to function as the carrier for the glycosaminoglycan residues should, of course, be substantially biologically inert after the coupling of the glycosaminoglycan or -glycans in question, in the sense that it should be devoid of at least interfering biological activity. As is readily understood, it should in order to permit coupling of a plurality of glycosaminoglycan residues be provided with a number of functional groups, such as e.g. amino, hydroxyl or carboxyl groups, distributed along the chain and capable of, after optional modification, being coupled to the glycosaminoglycan, either directly or via a coupling sequence. It is in this context to be noted that the glycosaminoglycan in question, depending on its preparation, may still have the terminal residue of its natural conjugate protein associated thereto, and that the binding then, of course, advantageously will take place via e.g. an amino acid in such a residue.

Further, the carrier polymer should preferably have a good solubility in water. At least it should, in accordance with what has previously been said about the conjugate, be at least substantially water-soluble after the coupling of the glycosaminoglycan groups. Specific polymer chains which may be suitable for the purposes of the invention will readily be apparent to the skilled person after having taken part of the general inventive concept. This is, of course, also the case for the degree of branching on the polymer chain that may be permitted within the scope of the expression "substantially linear".

Preferably, however, the polymer chain is a natural or synthetic polypeptide, polysaccharide or aliphatic polymer. As specific examples may be mentioned polylysine, polyornithine, chitosan, polyimine and polyallylamine.

With regard to the fact that it is usually desired that the glycosaminoglycan will maintain its biological activity after the binding to the polymer carrier, it is preferred that each glycosaminoglycan molecule is bound terminally and by only a single bond to the carrier polymer. Suitably, the glycosaminoglycan is bound via an amino acid, and then preferably a terminal amino acid, but also free amino groups of a glucosamine unit may be used. The latter may exist free as such or may have been liberated through desulphation or deacetylation.

The number of glycosaminoglycan residues per polymer backbone chain is, as mentioned above, at least 20, but preferably higher, usually at least 30. Depending on the polymer backbone chain used, it may be preferred to have at least 60 and even more than 100 glycosaminoglycan residues per polymer backbone chain, as will appear from the working examples presented further on. The upper limit depends on the circumstances and is set inter alia by the solubility properties of the selected carrier polymer, how high a viscosity that may be permitted, etc. In addition to the intended use of the specific conjugate, the optimum number of glycosaminoglycan units will also depend on the carrier polymer, and then particularly the size thereof. In the case of electrostatic binding of the conjugate to a substrate surface, which will be discussed in more detail below, the charge density of the substrate surface will, of course, also have to be considered. Thus, the glycosaminoglycan residues should not be located so closely that they will interfere with each other, but neither should they have too wide gaps between them. As an example it may be mentioned that e.g. polylysine as a carrier polymer should have a molecular weight higher than about 50,000. The suitable number of glycosaminoglycan residues for each specific carrier polymer and use, respectively, will, however, readily be determined by the skilled person.

Particularly in the case that an amino-functional polymer is used as the carrier, it may in some cases, especially when the polymer backbone chain is sparsely substituted with glycosaminoglycans, be favourable to block the remaining free amino groups, which, for example, may be effected by acetylation. An alternative approach might be to substitute a desired number of amino groups with e.g. methyl groups before attaching the glycosaminoglycans.

As already indicated, the novel conjugate according to the invention may be bound to a surface having affinity to the conjugate (usually but not necessarily to the glycosaminoglycan residues) so as to thereby provide the surface with the desired biological activity. According to a further aspect of the invention, such a prepared surface is accomplished by simply contacting, under suitable conditions, a biologically active conjugate comprising a substantially straight-chained organic polymer having a number of functional groups distributed along the polymer backbone chain, via which groups a number of molecules from the group of sulphated glycosaminoglycans are anchored by covalent bonds, with a surface having affinity to the conjugate.

Another aspect of the invention provides a substrate surface having affinity-bound thereto a biologically active conjugate comprising a substantially straight-chained organic polymer having a number of functional groups distributed along the polymer backbone chain, via which groups a number of molecules from the group of sulphated glycosaminoglycans are anchored by covalent bonds.

A preferred form of affinity between the conjugate and the substrate surface is of electrostatic nature, and more particularly that binding takes place by electrostatic interaction between the glycosaminoglycan residues and the substrate surface, as will be illustrated in more detail hereinafter.

Since the glycosaminoglycan molecules of a conjugate according to the invention are in great excess in relation to the carrier polymer, the conjugate may be regarded as a "macromolecular glycosaminoglycan". The number of anion groups per conjugate will thereby by far exceed the number existing per glycosaminoglycan molecule, which results in the conjugate, by virtue of its size, being capable of binding irreversibly to a cationic surface through ionic interaction. For the conjugate to be released from the surface, all glycosaminoglycan residues must, of course, be released from the surface simultaneously, which in contrast to the release of "free" glycosaminoglycan molecules will require a considerable supply of energy.

With the exception of certain situations which will be described further on, it is generally intended that the biological activity of the conjugate should be due to the glycosaminoglycan residues. In such a case, the number of glycosaminoglycan residues should be sufficient for a certain part of these residues per carrier polymer chain to be capable of together mediating a strong, irreversible binding to a surface which has been provided with cationic groups, while the remaining glycosaminoglycan chains freely can exert their biological activity by interacting with a biological tissue, e.g. the constituents of the blood.

Surface-preparation with a glycosaminoglycan according to the above is thus based upon a combination of covalent binding and ionic interaction, a considerable advantage being that the conjugate is prepared as an intermediate product, which means that all coupling chemistry may be made separately from the final product. Further, the final surface modification process becomes very simple and may be performed in a reproducible manner. For example, surface-heparinization with a heparin conjugate according to the invention therefore provides, as already mentioned, a considerably simplified method for efficient heparinization in relation to current methods for surface-heparinization. Notwithstanding the foregoing, it is, of course, possible to optionally carry out a cross-linking step after the affinity adsorption of the conjugate to the substrate surface in order to improve the stability of the heparinized surface even further.

A conjugate for use according to this particular aspect of the invention will thus have an electrostatic net charge which is sufficient to permit substantially irreversible binding to an oppositely charged substrate surface.

The substrate material to be surface-prepared, e.g. surface-heparinized, according to the above may in principle be any material that is desired to be made biocompatible, provided that its surface is or may be made cationic. As described previously, the invention may apply to a body-foreign material, such as various polymers, metals and ceramics. It may, however, also apply to an endogenous material, i.e. a tissue surface exhibiting affinity for the glycosaminoglycan in question. In this connection it is of interest to note that the healthy natural vessel wall in its outermost structure against the blood contains sulphated glycosaminoglycans having antithrombin-binding pentasaccharide sequences.

Various methods for making a substrate surface cationic are well known. Treatment with polyimine has proved to be a suitable method, but also other polyamines, such as e.g. polylysine, chitosan or polyallylamine, may be used, as will be described in the working examples below.

The novel glycosaminoglycan conjugate may within the scope of the invention also contain chains of one or more other substances bound to the carrier polymer in addition to the glycosaminoglycan chains, e.g. another biologically active substance. Such other biologically active substance may in that case be intended to act simultaneously with or separate from the glycosaminoglycan activity. In the latter case, only the biological activity of the complementary substance would be of interest, the glycosaminoglycans only being utilized for the affinity binding to the substrate surface. The conjugate according to the invention may thus also only function as a carrier for desired biologically active substances which one wants to bind to a surface. Examples of substances which in addition to the glycosaminoglycans may be bound to the polymer backbone chain are growth factors, enzymes, antibodies, matrix proteins, steroids, etc. It is in this context also to be noted that a conjugate with very specific adsorption properties may be accomplished, for example, with monoclonal antibodies as a complement to the glycosaminoglycan units.

Optionally, it may in the case of such combined conjugates be desired to suppress the biological activity of the glycosaminoglycan itself, which, for example, in the case of the coagulation inhibiting activity of heparin may be effected by desulphation. In such a case, the biological activity of the conjugate would thus be completely linked to the activity of complementary substances which are bound to the polymer backbone chain.

While in many cases it is the surface-binding effect of the conjugate that is essential, not to say necessary, this effect is, however, in certain cases of less interest, and it may even for some applications be desired to suppress it more or less completely. In the same way it may, as mentioned above for the combined conjugates, also in the case of a pure glycosaminoglycan conjugate be desired to eliminate or at least reduce the biological activity of the glycosaminoglycans. In some cases, such as e.g. for heparin, the glycosaminoglycan may have several different biological effects, and depending on the intended application, one biological activity may then be suppressed in favour of another. For example, in the case of heparin the anticoagulating effect thereof may as above be inhibited by desulphation, while another biological activity which is not linked to the previously mentioned pentasaccharide unit will remain unaffected.

As appears from the above, the composition of the novel conjugate may thus be varied within wide limits to be adapted to different application fields.

Another aspect of the invention relates to the production of the described conjugate by providing a substantially straight-chained organic polymer having a number of functional groups distributed along the polymer backbone chain, and to these functional groups, optionally via a coupling reagent, covalently binding a number of molecules from the group of sulphated glycosaminoglycans in a non-active part thereof. This may within the scope of the invention be performed in several different ways.

Thus, the glycosaminoglycan may, for example, be bound directly to an amino-functional polymer chain utilizing a nitrous acid degraded glycosaminoglycan having a terminally located aldehyde group prepared according to the method described in U.S. Pat. No. 4,613,665. This method involves, however, a restriction to a partially degraded glycosaminoglycan, and the degree of substitution is difficult to control. Also, practical difficulties arise due to the fact that the polymer is easily precipitated by the glycosaminoglycan.

According to a preferred method, the glycosaminoglycan is instead bound to the polymer chain by means of a coupling reagent, and preferably a heterobifunctional one. It may be noted that bifunctional coupling reagents for e.g. hydroxyl or amino groups can, however, generally not be used, since they will lead to intra- as well as inter-molecular cross-linking with consequential blocking and aggregation, respectively.

As an example of how a conjugate according to the invention may be prepared, the coupling of heparin to a polylysine will now briefly be described. By selecting a polylysine having a molecular weight above 400,000, a synthetic proteoglycan having up to 500 heparin chains per carrier molecule may be prepared. A hetero-bifunctional coupling reagent suitable for this purpose, N-succinimidyl-3-(2-pyridyldithio)-propionate (SPDP), is coupled to amino groups on the polylysine, the SPDP-substituted polylysine then being purified chromatographically. In a separate coupling step, SPDP is also coupled to amino groups on heparin which are present either in terminal amino acid residues or as free glucosamine (the latter content may be controlled via N-desulphation or N-deacetylation). The SPDP-groups are reduced to thiol function, whereupon the SH-substituted heparin is purified chromatographically. The content of SPDP groups in polylysine and SH-groups in heparin, respectively, are determined spectrophotometrically, and heparin is mixed with polylysine in an equimolecular amount with regard to SPDP and SH, heparin being bound covalently to polylysine via disulphide exchange, the reaction rate of which may be followed spectrophotometrically. It has surprisingly been found that the precipitation reaction between polylysine and heparin does not take place when polylysine has been provided with SPDP-groups, even if only a certain portion of the amino groups of polylysine have been substituted. Nevertheless, practical experiments have shown that the disulphide exchange is quicker and proceeds to completion only at a high salt concentration (suitably 3M NaCl). When the reaction is completed, the conjugate is purified chromatographically, free heparin and low-molecular reaction products being removed.

Concerning the stability of the thus prepared heparin conjugate in different environments, it has surprisingly been found that the obtained disulphide bridges which couple heparin to the polymer backbone chain cannot be cleaved with glutathione but only with low-molecular non-physiological thiol reagents, such as e.g. mercaptoethanol.

It is further to be noted that a substantial advantage of heparinizing with a heparin conjugate according to the invention resides in the possibility of starting from a less processed heparin raw material than in the conventional processes.

The invention is illustrated further in the following Examples.

EXAMPLE 1

Preparation of conjugates and test of surface-bound biological activity

Two different batches of heparin (Heparin, Kabi Pharmacia AB, Sweden, molecular weight about 12,000) was used. The content of amino acids and the relative occurrence of free primary amino groups were analysed, the following results being obtained.

|  | Amino acid nitrogen (µg/ml) | Total nitrogen (µg/ml) | Primary amine (rel. scale) |
| --- | --- | --- | --- |
| Heparin A | 0.36 | 5.38 | 5,000 |
| Heparin B | 0.08 | 5.37 | 340 |

Since heparin B exhibited a very low content of free amine, N-desulphation according to the method described by Yuko Inone et al., Carbohydrate Research, 46 (1976) 87–95, was performed. After carried out N-desulphation, the value 18,000 on the relative scale for primary amine was obtained.

Heparin A and heparin B (desulphated) were dissolved in phosphate buffer, pH 7.5, (200 mg/4 ml), to which 1 ml of SPDP (10 mg/ml MeOH) was added under stirring, and the reaction was allowed to proceed for 20 minutes. The SPDP-substituted heparin thus obtained was purified on Sephadex® G-25 (Pharmacia LKB Biotechnology AB, Sweden). To 100 µl of the obtained sample were added 900 µl of dithiothreitol (DTT, 10 mg/ml), and the obtained absorbance was measured spectrophotometrically at 343 nm. The substitution-degree for heparin A was 0.21 and for heparin B (desulph.) 0.17. SPDP coupled to heparin was reduced to SH by the addition of DTT and subsequent chromatographical purification.

Polylysine having a molecular weight of 450,000 was dissolved in water (20 mg/3 ml), to which 2 ml of SPDP (10 mg/ml MeOH) were added, and the reaction was allowed to proceed under shaking for 20 minutes. Purification was performed on Sephadex® G-25 (Pharmacia LKB Biotechnology AB, Sweden) with 0.15M NaCl as eluent. The void fraction was tested with DTT, the substitution-degree being determined as 158 SPDP-groups per molecule of polylysine.

The above prepared solutions of heparin-SH and polylysine-SPDP, respectively, were adjusted to 3M NaCl and mixed in such proportions that a ten percent excess of SH-groups in relation to SPDP-groups was obtained, and the reaction was allowed to proceed overnight. Both preparations (heparin A and heparin B (desulph.)) had then proceeded to completion, which was determined by spectrophotometrical measurement of the release of thiopyridone at 343 nm. The preparations were purified on sephacryl® S-500 (Pharmacia LKB Biotechnology AB, Sweden) with 0.5M NaCl as eluent, the heparin-polylysine conjugates emerging as a void peak with baseline separation to free heparin. The content of heparin was determined with the Orcinol assay described in Larsson, R., et al., Biomaterials 10 (1989) 511–516.

The respective heparin conjugates were then diluted to 50 µg heparin/ml in citrate buffer, pH 3.8, with addition of 0.5M NaCl. Tubings of polyethylene (PE) were surface-heparinized by treatment as follows:

1) Ammonium persulphate (1%, 60° C., 120 min.)
2) Polyethylene imine (0.3 mg/ml, RT, 15 min.).
3) Heparin conjugate solution as above (RT, 120 min.).

The tubings were finally flushed with borate buffer, pH 9, 2×10 min., and water.

The surface-heparinized tubings were tested with regard to the inhibiting capacity of thrombin according to the following method. The tubings were first rotated with human plasma during 90 minutes, whereupon they were rinsed with sodium chloride solution. Then the tubings were incubated with a solution of thrombin (15 U/ml, 10 min., RT, under rotation) and rinsed with sodium chloride solution. Half of the tubings were then incubated with defibrinogenated plasma for 60 seconds. Surface-bound thrombin activity was measured by incubating the tubings with a chromogenic substrate for thrombin during 60 seconds, after which the reaction was stopped by the addition of citric acid. The obtained absorbance was measured at 405 nm. The following values were obtained.

|  | Conjugate with Heparin A | Conjugate with Heparin B (desulph.) |
| --- | --- | --- |
| Uptake of thrombin (without defib. plasma) | 0.639 ± 0.050 | 0.611 ± 0.156 |
| Residual amount of thrombin (with defib. plasma) | 0.003 ± 0.001 | 0.006 ± 0.001 |

The results indicate that both preparations provided a perfectly satisfactory effect with regard to uptake and inhibition of thrombin.

EXAMPLE 2

Preparation of conjugates with different substitution-degrees and test of surface-bound biological activity A conjugate, called Conjugate I, was prepared as described in Example 1. The final substitution-degree of heparin per polylysine was 240:1.

Then another conjugate, called Conjugate II, was prepared. In this case the starting material was a polylysine with a higher substitution-degree of SPDP, prepared by adjustment of the pH to 8 in the polylysine solution before the addition of SPDP. The substitution-degree was determined as 633 SPDP-groups per polylysine molecule.

Heparin-SH was prepared as in Example 1 and was reacted with the highly substituted polylysine obtained above. The reaction proceeded to 77 % conversion, and the substitution-degree of heparin per polylysine was therefore 490:1. Tubings of polyethylene (PE) were prepared and tested as described in Example 1, the following results being obtained.

|  | Conjugate I | Conjugate II |
| --- | --- | --- |
| Uptake of thrombin (without defib. plasma) | 0.516 ± 0.021 | 0.526 ± 0.031 |
| Residual amount of thrombin (with defib. plasma) | 0.011 ± 0.001 | 0.008 ± 0.001 |

The results indicate that both conjugates provided satisfactory results.

EXAMPLE 3

Test of surface-heparinised extra-corporeal system

An extra-corporeal system composed of the following components was used: Drainage catheter (polyvinyl chloride (PVC)), arterial cannula (PVC+steel), tubing set (PVC), pump bladder (ethylbutyl acrylate), valves (polypropylene (PP)+PE), oxygenator (polycarbonate+hollow-fibres of PP).

All the components were surface-heparinized by treatment in three steps:

1) Ammonium persulphate (1%, 60° C., 120 min.)

2) Polyethylene imine (0.3 mg/ml, borate buffer, pH 9, RT, 15 min.)

3) Heparin-polylysine conjugate, prepared according to Example 1, was diluted to 30 µg/ml in citrate buffer, pH 3.8, with 0.5M NaCl, and was treated at room temperature for 120 minutes. The components were finally rinsed 2×15 min. with borate buffer, pH 9, and water. After drying, sterilization with ethylene oxide was carried out.

The extra-corporeal system was connected to an anaesthetized pig which had not received any anti-coagulant therapy for partial by-pass between the right atrium and the aorta. The external system continuously pumped about three liters per minute during twenty-four hours without any problems with clogging due to coagulation. The coagulation time was all the time at a constant value, indicating that there was no release of heparin to the blood path.

The results demonstrate that a complete system for extra-corporeal support circulation easily may be surface-heparinized with the heparin conjugate to obtain a stable, well-functioning heparin surface, which may be sterilized with ethylene oxide.

EXAMPLE 4

Test of biological activity of various heparin-conjugates in solution

Heparin-polylysine conjugates with different substitution-degrees were prepared according to Examples 1 and 2. The biological activity of the conjugates was determined with regard to their capability of inhibiting Factor Xa and thrombin in buffer solution containing antithrombin or in plasma. The results obtained were compared with corresponding standard graphs obtained by the addition of known amounts of heparin having a known specific biological activity (180 I.U./mg). The following results were obtained.

| Conjugate | Biological activity I.U./mg heparin | | | | |
|---|---|---|---|---|---|
| | Heparin/ polylysine | Xa/AT | Xa/ Plasma | Tr./AT | Tr./Plasma |
| I | 235 | 116 | 95 | 48 | 45 |
| II | 490 | 61 | 29 | 10 | 20 |
| III | 550 | 10 | 43 | 18 | 25 |

The results indicate that the described process may be utilized to prepare conjugates having a high as well as a low biological activity.

EXAMPLE 5

Effect of different polylysine sizes

Five different batches of polylysine with the respective molecular weights 13,000, 64,000,, 98,000, 249,000 and 464,000 were modified with SPDP in accordance with Example 1, the following substitution-degrees (SPDP-groups per molecule of polylysine) being obtained:

| Sample | Molecular weight | Substitution-degree |
|---|---|---|
| I | 13,000 | 6 |
| II | 64,000 | 31 |
| III | 64,000 | 45 |
| IV | 98,000 | 35 |
| V | 249,000 | 87 |

-continued

| Sample | Molecular weight | Substitution-degree |
|---|---|---|
| VI | 464,000 | 158 |

Heparin, having the value of 7,000 on the relative scale for primary amine, was modified with SPDP for the introduction of free thiol groups in accordance with Example 1, substitution-degrees of 0.2–0.3 being obtained. Respective conjugates were prepared according to Example 1. Separation was performed on a column with sephacryl® S-300 or Sephacryl® S-400 (Pharmacia LKB Biotechnology AB, Sweden) as the separation medium. Conjugate I could not be separated from free heparin. For the other conjugates satisfactory separation was obtained, and the conjugates obtained could be used for surface-heparinizing tubings according to Example 1. Testing with regard to uptake and inhibition of thrombin (according to Example 1) gave the following results:

| Conjugate | Uptake of thrombin (without def. plasma) | Residual amount of thromin (with def. plasma) |
|---|---|---|
| I | — | — |
| II | 0.012 ± 0.006 | 0 |
| III | 0.086 ± 0.047 | 0 |
| IV | 0.494 ± 0.009 | 0.003 |
| V | 0.532 ± 0.043 | 0.005 |
| VI | 0.490 ± 0.004 | 0.004 |

The results indicate that conjugates II–VI may be used according to the invention to prepare surfaces with heparin activity. However, conjugates IV–VI give the best results.

EXAMPLE 6

Preparation of conjugate with chitosan as carrier substance

Chitosan (SeaCure 110L, viscosity <20 mPas, molecular weight about 120,000, Protan Biopolymer A/S, Drammen, Norway) was dissolved to 10 mg/ml in water with 1% acetic acid. To 1.5 ml solution was added 1.0 ml SPDP (10 mg/ml MeOH) under stirring at 50° C., and the reaction was allowed to proceed for one hour. The sample was loaded on a PD-10 column (Pharmacia LKB Biotechnology AB, Sweden) and eluted with 0.5M NaCl with 1% acetic acid. The void fraction was collected and analysed for presence of SPDP. The content of SPDP was determined as 0.972 µmole/ml, corresponding to about 40 SPDP-groups per chitosan molecule.

Heparin was prepared with free thiol groups according to Example 1. To the obtained heparin solution was then added sodium chloride to a final concentration of 3.5M. The heparin solution was then added to the first prepared chitosan-SPDP solution under vigorous stirring, and the reaction was allowed to proceed at room temperature overnight. Spectrophotometrical control indicated that the reaction had proceeded to 100 %. The solution was fractionated on Sephacryl® S-300 (Pharmacia LKB Biotechnology AB, Sweden) and the void fraction was collected. Tubings of Pebax® (polyether block amide from Atochemie, France) were prepared for thrombin test according to Example 1. The following results were obtained:

| Uptake of thrombin (without def. plasma) | Residual amount of thrombin (with def. plasma) |
| --- | --- |
| 0.491 ± 0.016 | 0.002 |

The results demonstrate that a surface prepared with a chitosan-heparin conjugate gives a perfectly satisfactory effect.

EXAMPLE 7

Preparation of conjugates with polyallylamine

Polyallylamine hydrochloride (Aldrich, molecular weight about 50,000), 10 mg, was dissolved in 1.5 ml of borate buffer, pH 9, to which 1.0 ml SPDP (10 mg/ml MeOH) was added under stirring and reacted for 30 minutes. The solution was loaded on a PD-10 column, which was eluted with 0.9% NaCl. The void fraction was collected, and analysis indicated that it contained 8.46 μmole/ml SPDP, corresponding to about 192 SPDP-groups per molecule of polyallylamine. This product was used below for the preparation of Conjugate I.

Another 10 mg of polyallylamine hydrochloride, dissolved in water instead of borate buffer, were SPDP-substituted in the same way as above. The void fraction then contained 1.56 μmole SPDP/ml, corresponding to 32 SPDP-groups per molecule of polyallylamine. This product was then used for the preparation of Conjugate II below.

Another preparation utilized polyallylamine hydrochloride which had been partially methylated by reacting 2 μmole of polyallylamine dissolved in 7 ml of water with the pH adjusted to 3.5 with 861 μmole of formaldehyde in the presence of 1610 μmole of cyanoborohydride. After reaction over night, the modified polyallylamine was purified on Sephade® G-25 (Pharmacia LKB Biotechnology AB, Sweden). Modified polyallylamine hydrochloride, 10 mg, was dissolved in borate buffer, pH 8, and was substituted with SPDP as described above. The void fraction then contained 1.5 μmole/ml, corresponding to about 50 SPDP groups per molecule of polyallylamine. This product was then used for the preparation of Conjugate III below.

Heparin was prepared with free thiol groups according to Example 1, whereupon the resulting heparin-SH was mixed with the respective polyallylamine-SPDP products in an equimolecular relation with regard to SH- and SPDP-groups. After reaction for one hour the salt content was raised to 3M, and the reaction was allowed to proceed overnight at room temperature. The reaction yield was more than 95% for all three reactions. The respective reaction solutions of Conjugates I and II were adjusted with 10M sodium hydroxide to pH 10, and 100 μl of acetic anhydride were then added under vigorous stirring in order to acetylate the remaining amino groups. The heparin conjugates obtained, Conjugate I, Conjugate II and Conjugate III, respectively, were purified on a Sephacryl® S-400 column (Pharmacia LKB Biotechnology AB, Sweden), the conjugates being obtained in the void fraction.

Tubings of polyethylene were prepared with the three obtained heparin conjugates for the thrombin test according to Example 1, the following results being obtained.

| | Uptake of thrombin (without defib. plasma) | Res. amount of thrombin (with defib. plasma) |
| --- | --- | --- |
| Conjugate I | 0.437 ± 0.008 | 0.007 ± 0.002 |
| Conjugate II | 0.445 ± 0.020 | 0.003 ± 0.001 |
| Conjugate III | 0.501 ± 0.032 | 0.005 ± 0.002 |

The results demonstrate that all three conjugates give a perfectly satisfactory effect.

EXAMPLE 8

Preparation of surfaces with different amino-functional substrate surfaces

Tubings of polyethylene were heparinized as follows, the added designations A, B, C and D, respectively, indicating alternative amino-functionalizing treatments of the tubing surface:

1. Ammonium persulphate (1%, 60° C., 60 min.)
2A. Polyethylenimine (0.3 mg/ml, borate pH 9, RT, 15 min.)
2B. Polyallylamine (10 mg/ml, borate pH 9, RT, 15 min.)
2C. Chitosan (10 mg/ml, 1% HAc, RT, 15 min.)
2D. Polylysine (5 mg/ml in water, RT, 15 min.)
3. Heparin-polylysine conjugate prepared according to Example 1 (50 μg/ml in citrate buffer, 0.5M NaCl, pH 3.8, RT, 120 min.).

The surfaces thus prepared were thoroughly rinsed with borate buffer, pH 9, and water.

Polyethylene tubings heparinized according to the above four alternatives were tested with regard to uptake and inhibition of thrombin, as described in Example 1, all the alternatives exhibiting a perfectly satisfactory effect.

EXAMPLE 9

Surface-heparinization of a lens (PMMA) and test of platelet adhesion

Intraocular lenses of polymethyl methacrylate (PMMA) were heparinized according to Example 1 and then tested with regard to adhesion of platelets.

Non-modified and surface-heparinized lenses, respectively, were incubated in fresh human citrated whole blood under constant motion for 60 minutes. The lenses were then rinsed repeatedly in sodium chloride solution to remove all adhering blood. Finally, adenosine triphosphate (ATP) was extracted from any platelets which had adhered to the lens surface, and the content of ATP obtained was determined by bioluminescence. Platelet adhesion to the heparinized lenses was reduced with 98 % compared with the untreated control lenses.

EXAMPLE 10

Adsorption of heparin conjugate to a "biological surface"

In order to examine whether a heparin conjugate prepared according to the present invention can be adsorbed irreversibly to a surface coated with thrombotic biological material the following experiments were carried out:

Non-surface-modified tubings of polyethylene were half-filled with citrated whole blood and rotated for 60 minutes. The tubings were then drained of blood and thoroughly rinsed with sodium chloride solution. Hereby the tubings were coated with thrombotic material consisting of plasma proteins and platelets in different activation stages. Heparin-polylysine conjugate prepared according to Example 1 was diluted to a final concentration of 100 μg/ml in sodium chloride solution, which solution then was rotated in the tubings for 60 minutes. The tubings were finally thoroughly rinsed with borate buffer, pH 9, and water.

The tubings thus heparinized were tested with regard to uptake and inhibition of thrombin according to Example 1, the test tubings exhibiting a perfectly satisfactory effect.

EXAMPLE 11

Combination preparation with urease

Polylysine (10 mg, molecular weight 464,000) was dissolved in 1.5 ml water, to which 1.0 ml of SPDP (10 mg/ml MeOH) was added under shaking, and the reaction was then allowed to proceed for 30 minutes. The sample was loaded on a PD-10 column and eluted with 0.9 % NaCl. The void fraction was collected, and analysis indicated that the content of SPDP was 1.053 µmole/ml.

Urease (U-1500, from jackbean, Sigma, USA) was dissolved to 10 mg/ml in phosphate buffer, pH 7.5, and filtrated through a 0.22 µm filter. The content of free SH-groups was determined as 0.161 µmole/ml.

Polylysine-SPDP dissolved in 3M NaCl was mixed with urease, such that about 10% of available SPDP-groups could undergo disulphide exchange with SH-groups of the urease. Spectrophotometrical measurement at 343 nm confirmed that this had taken place. Then, heparin modified with free SH-groups according to Example 1 was added, the amount of added heparin-SH corresponding to the remaining 90 % of available SPDP-groups. The reaction proceeded to completion. The obtained conjugate was finally purified on a Sephacryl® S-400 column (Pharmacia LKB Biotechnology AB, Sweden), the conjugate being obtained in the void fraction. Testing of the obtained conjugate indicated that heparin activity as well as urease activity could be detected.

We claim:

1. A water-soluble conjugate having antithrombin-binding activity comprising a biologically inert carrier in the form of a substantially straight-chained organic polymer selected from the group consisting of polylysine, polyornithine, a polysaccharide and an aliphatic polymer, having chemically reactive groups distributed along the polymer backbone chain, and at least 30 molecules of sulphated glycosaminoglycan anchored to the chemically reactive groups through covalent bonds, wherein each sulphated glycosaminoglycan molecule is bound to the polymer backbone chain via a single point of attachment in a part of the sulphated glycosaminoglycan molecule that is not responsible for said antithrombin-binding activity, such that after anchoring of said molecule of sulphated glycosaminoglycan to said chemically reactive group, the molecule of sulphated glycosaminoglycan retains said antithrombin-binding activity.

2. The conjugate according to claim 1, wherein said substantially straight-chained organic polymer chain is polylysine, polyornithine, chitosan, polyimine or polyallylamine.

3. The conjugate according to claim 1, or 2, wherein some or all of the molecules of sulphated glycosaminoglycan are bound to the polymer backbone chain via the terminal end of the sulphated glycosaminoglycan molecule.

4. The conjugate according to claim 1, wherein the sulphated glycosaminoglycan molecules are bound to the polymer backbone chain via an amino group of the sulphated glycosaminoglycan molecule.

5. The conjugate according to claim 1, having at least 100 glycosaminoglycan molecules.

6. The conjugate according to claim 1, wherein said sulphated glycosaminoglycan molecule is heparin or a fragment thereof.

7. The conjugate according to claim 1, said sulphated glycosaminoglycan molecules being bound to the polymer backbone chain via a coupling reagent.

8. The conjugate according to claim 7, wherein said coupling reagent is a heterobifunctional coupling reagent.

9. The conjugate according to claim 1, said substantially straight-chained organic polymer further having at least one biologically active substance attached to the polymer backbone chain.

10. A therapeutical composition comprising:

the water-soluble conjugate according to any one of claims 1 or 2; and a biologically active substance.

11. A process of preparing a water-soluble conjugate having antithrombin-binding activity, said water-soluble conjugate having a biologically inert carrier in the form of a substantially straight-chained organic polymer selected from the group consisting of polylysine, polyornithine, a polysaccharide and an aliphatic polymer, having chemically reactive groups distributed along with polymer backbone chain and at least 30 molecules of sulphated glycosaminoglycan anchored to the chemically reactive groups through covalent bonds, wherein each sulphated glycosaminoglycan molecule is bound to the polymer chain via a single point of attachment, such that after anchoring of said molecule of sulphated glycosaminoglycan to said chemically reactive group, the molecule of sulphated glycosaminoglycan retains said antithrombin-binding activity, comprising reacting a hetero-bifunctional coupling reagent with chemically reactive groups on both the sulfated glycosaminoglycan molecules and the polymer backbone chain, with the proviso that said reacting with said chemical reactive groups on the sulfated glycosaminoglycan molecules takes place in a part of the sulphated glycosaminoglycan molecule that is not responsible for said antithrombin-binding activity.

12. A prepared substrate surface comprising an antithrombin-binding active conjugate affinity-bound to a substrate surface, said antithrombin-binding active conjugate comprising a substantially straight-chained organic polymer having functional groups distributed along the polymer backbone chain and at least 30 sulphated glycosaminoglycan molecules anchored to the functional groups through covalent bonds.

13. A process of preparing a surface with sulphated glycosaminoglycan, comprising the step of contacting a polyanionic conjugate of a substantially straight-chained organic polymer having chemically reactive groups distributed along the polymer backbone chain and at least 30 sulphated glycosaminoglycan molecules anchored, via a single point of attachment in a part of the sulfated glycosaminoglycan molecule that is not responsible for antithrombin-binding activity, to the chemically reactive groups through covalent bonds, with a cationic substrate surface having affinity to the polyanionic conjugate, such that the polyanionic conjugate is bound to said cationic substrate surface by electrostatic interaction.

* * * * *